United States Patent [19]
Feeney et al.

[11] Patent Number: 5,508,610
[45] Date of Patent: Apr. 16, 1996

[54] ELECTRICAL CONDUCTIVITY TESTER AND METHODS THEREOF FOR ACCURATELY MEASURING TIME-VARYING AND STEADY STATE CONDUCTIVITY USING PHASE SHIFT DETECTION

[75] Inventors: Robert K. Feeney, Acworth; Ajeet Rohatgi, Marietta; David R. Hertling, Stone Mountain, all of Ga.

[73] Assignee: Georgia Tech Research Corporation, Atlanta, Ga.

[21] Appl. No.: 985,635

[22] Filed: Dec. 3, 1992

[51] Int. Cl.$^6$ .................. G01N 27/72; G01R 33/12; G01R 31/26
[52] U.S. Cl. .................. 324/233; 324/227; 324/719; 324/765
[58] Field of Search .................. 324/233, 719, 324/165 R, 158 D, 750, 765, 641, 709, 227

[56] References Cited

U.S. PATENT DOCUMENTS

| | | | |
|---|---|---|---|
| 3,805,160 | 4/1974 | Philbrick et al. | 324/158 |
| 3,890,564 | 6/1975 | Watanabe et al. | 324/40 |
| 3,953,796 | 4/1976 | Keller | 324/158 |
| 4,059,795 | 11/1977 | Mordwinkin | 324/233 |
| 4,074,186 | 2/1978 | Flaherty | 324/709 |
| 4,303,885 | 12/1981 | Davis et al. | 324/237 |
| 4,424,486 | 1/1984 | Denton et al. | 324/225 |
| 4,475,083 | 10/1984 | Linder | 324/227 |
| 4,651,093 | 3/1987 | Detriche et al. | 324/232 |
| 5,017,869 | 5/1991 | Oliver | 324/230 |
| 5,045,789 | 9/1991 | Inoue et al. | 324/255 |
| 5,055,784 | 10/1991 | Jaeger et al. | 324/233 |

OTHER PUBLICATIONS

Ciszek, T. F., et al., "Some Effects of Crystal Growth Parameters on Minority Carrier Lifetime in Float–Zoned Silicon," *J. Electrochem Soc.*, vol. 136, No. 1, Jan. 1989, pp. 230–234.

Pang, S. K., et al., "Effect of Oxygen Concentration on Lifetime in Magnetic Czochralski Silicon," *J. Electro–chem Soc.*, vol. 138, No. 2, Feb. 1989, pp. 523–527.

Pang, S. K., et al., "Record high recombination lifetime in oxidized magnetic Czochralski silicon," *Appl. Phys. Lett.*, vol. 59, No. 2, Jul. 8, 1991, pp. 195–197.

*Primary Examiner*—Walter E. Snow
*Attorney, Agent, or Firm*—Hopkins & Thomas; Scott A. Horstemeyer

[57] ABSTRACT

An electrical conductivity tester accurately measures the time-varying electrical conductivity $\sigma(t)$ and steady-state electrical conductivity $\sigma_{ss}$ of a test material. In a first embodiment, the transmission phase of a probe circuit is monitored to determine the conductivity of a test material. In the first embodiment, an oscillator circuit generates a reference oscillator signal. A probe circuit receives the reference oscillator signal, magnetically couples to the test material, and modifies the reference oscillator signal via electromagnetic induction to derive a modified transmission phase signal. Finally, a phase detector circuit derives a transmission phase signal by combining the reference oscillator signal and the modified transmission phase signal, the transmission phase signal being directly convertible to the conductivity. In a second embodiment, an amplifier is connected to the probe circuit to form an oscillator circuit. The oscillator circuit generates an oscillator signal in response to the magnetic coupling of the probe circuit with the test material. A frequency discriminator generates a frequency signal from the oscillator signal, the frequency signal being convertible to the conductivity.

35 Claims, 4 Drawing Sheets

ELECTRICAL CONDUCTIVITY TESTER AND METHODS THEREOF FOR ACCURATELY MEASURING TIME-VARYING AND STEADY STATE CONDUCTIVITY USING PHASE SHIFT DETECTION

FIELD OF THE INVENTION

The present invention generally relates to measuring the electrical conductivity of a test material, such as a conductor, semiconductor, or dielectric, and more particularly, to an electrical conductivity tester and associated methods for measuring the time-varying as well as steady-state conductivity of a test material without destruction or physical contact with the test material.

RELATED ART

The measurement of the conductivity σ (inverse of resistivity) of a material yields many important characteristics. For instance, impurities, defects, hardness, thickness, stress levels, charge carrier (holes or electrons) doping levels, charge carrier lifetime τ charge carrier traps, and other properties, can be identified and specifically located. These characteristics are important in quality control and in experimental research when determining whether a fabrication process for a particular test material is satisfactory. As an example, these characteristics can be particularly useful in the manufacture of high quality silicon wafers for power-generating solar panels.

According to a now archaic, prior art technique for measuring conductivity, a plurality of sharply-pointed probes were pressed against a test material to pass a current through the test material. The voltages across the probes were then monitored along with the current flow so as to derive impedances. The conductivity of the test material could then be determined from the derived impedances. However, in the contact techniques, because sharply pointed ends of the probes were pressed against the surface of the test material, the crystal structure of the test material was often damaged or destroyed. Furthermore, the contact techniques are tedious and often inconvenient for use in automated manufacturing schemes.

As a result, other techniques were developed for permitting analysis without destruction or physical contact with the test material. The use of electromagnetic signals for measuring the conductivity of a test material has become prominent in the industry. Generally, in most conventional electromagnetic techniques, eddy currents are generated in the test material by electromagnetic induction from an adjacent probe coil excited by an alternating current. In turn, the eddy currents generate a magnetic field which couples to the probe coil and induces voltages within the probe coil. The sensitivity of the probe is at a maximum when the circuit is tuned to resonance.

The induced voltages in the probe coil are at substantially the same frequency as the excitation current, but are at a different phase angle and/or voltage amplitude. Essentially, the phase angle and voltage amplitude of the induced voltage depend upon the physical characteristics of the test material and the magnetic coupling between the test material and the probe coil. With the latter held constant, conductivity values and other physical characteristics can be determined from the induced voltages. Conventionally, the induced voltage is detected and measured as a variation in (1) power level $P_0$, (2) voltage amplitude $V_0$, (3) equivalent impedance $Z_0$ at the probe coil.

A common electromagnetic technique for measuring conductivity by monitoring the power level $P_0$ involves monitoring the quality factor Q of a probe coil. The quality factor Q of any coil is defined as follows.

$$\text{quality factor } Q = \frac{2\pi f \text{ (peak energy stored)}}{\text{(average power dissipated)}} = \frac{2\pi f L}{R_{\text{eff}}}$$

The quality factor Q is proportional to the ratio of the inductive reactance $2\pi f$ (f=operating frequency) of the coil and inversely proportional to the effective resistance $R_{\text{eff}}$. The effective resistance $R_{\text{eff}}$ includes the actual resistance of the coil and the other losses associated with the circuit. In conductivity determinations that measure the quality factor Q, losses within the test material are magnetically coupled into the coil. Thus, the measured quality factor Q of the coil changes in response to the conductivity σ of the test material.

Examples of apparatuses which employ Q techniques to measure conductivity σ are described in, for instance, U.S. Pat. Nos. 3,805,160 to Philbrick and 2,859,407 to Hanish, both the disclosures of which are incorporated herein by reference. These apparatuses are often referred to as "Q meters". In Q techniques, a series circuit comprising a probe coil and a variable capacitor is connected across an oscillator. The voltage across the variable capacitor is monitored to derive the conductivity. The variable capacitor is adjusted to cause the series circuit to resonate at a selected frequency. In operation, the oscillator frequency is adjusted to the selected frequency, and the power level of the oscillator is adjusted to some convenient Q value. The energized coil propagates electromagnetic signals in response to the oscillator signal. The conductivity of the test material is measured by monitoring the change of the quality factor Q of the probe coil when the test material is placed in close proximity to the probe coil. Furthermore, the sensitivity of the Q-measuring apparatuses is directly proportional to the unloaded Q-values of the respective probe coils.

An electromagnetic technique for determining conductivity by analyzing equivalent impedances $Z_0$ involves employing an impedance bridge as the probe. The magnitude and phase of the error voltage from the bridge is a measure of the conductivity. Bridge networks for measuring eddy currents are described in, for example, U.S. Pat. Nos. 2,084,836 to Buschbeck, 3,890,564 to Watanabe et al., 4,303,885 to Davis et al., 4,651,093 to Detriche et al., and 5,107,869 to Oliver, which disclosures are incorporated herein by reference as if set forth in full hereinbelow.

Another electromagnetic technique for measuring conductivity via equivalent impedances $Z_0$ involves using one or more probe coils and quadrature synthesis. Quadrature synthesis techniques do not use an impedance bridge, but require the creation of two quadrature phase signals representing the voltage signal driving a probe. Various combinations of the two phase shifted signals are used with an output signal from the probe to create signals for driving a display or other device which indicates relative impedance changes. Like the impedance bridge technique, the output signal is proportional to a change in probe impedance.

Quadrature synthesis techniques are employed in U.S. Pat. Nos. 2,561,182 to Crane, 3,046,479 to Mead et al., 3,441,745 to Reeves et al., 3,510,769 to Landee, 3,85,160 to Philbrick et al., 3,895,294 to Vinding, 4,303,885 to Davis et al., 4,424,486 to Denton et al., and 4,475,083 to Linder, which disclosures are incorporated herein by reference. In general, the apparatuses described by the foregoing U.S. patents require more than one probe coil. Moreover, several describe a multifrequency eddy current testing system wherein two or more frequencies are utilized with a common probe coil to derive conductivity measurements.

Conventional electromagnetic techniques for determining conductivity by analyzing variations in voltage amplitude $V_0$ involves employing one or more probe coils. U.S. Pat. Nos. 5,045,789 to Inoue et al. and 5,05,784 to Jaeger et al. (calibrating resistor in probe), both of which are incorporated herein by reference, describe systems for monitoring the voltage amplitude changes at the probe coil(s).

Although the prior art techniques and devices heretofore serve many useful purposes, these techniques are limited to narrow conductivity ranges, and none can accurately measure time-varying conductivity $\sigma(t)$ and transient conductivity $\sigma_{tr}(t)$, if at all. In the context of this document, "time-varying conductivity", or $\sigma(t)$, refers to the conductivity $\sigma$ of a test material as the conductivity $\sigma$ changes with time. "Transient conductivity", or $\sigma_{tr}(t)$, refers to the time-varying conductivity $\sigma(t)$ of a test material during the short time period directly after stimulation from an energy source, such as a light source, until the test material reaches a steady-state quiescent condition. Moreover, "steady-state conductivity", or $\sigma_{ss}$, refers to the conductivity $\sigma$ (perhaps time-varying or constant) of a test material while in a steady-state quiescent condition. Because prior art techniques cannot accurately measure time-varying conductivity $\sigma(t)$ and particularly transient conductivity $\sigma_{tr}(t)$, information regarding the charge carriers within a test material is severely limited. Specifically, using conventional techniques, it is virtually impossible to accurately measure the following attributes: total carrier (electrons or holes) lifetime $\tau$, the trap lifetime $\tau_{srh}$, the trap assisted Auger coefficient B, the auger recombination coefficient C, the surface recombination velocity, and the energy level corresponding to a trap. The inability to obtain the preceding information is an extreme limiting factor in semiconductor development and manufacture.

The prior art conductivity measurement techniques suffer from other inadequacies as well. They are undesirably susceptible to adverse variation by interference or noise, especially those techniques related to monitoring amplitude variations $V_0$. Moreover, the speed with which conductivity values are determined is rather slow. Finally, the prior art techniques usually require a nulling circuit which adds to circuit complexity which may adversely affect the results and the reliability.

SUMMARY OF THE INVENTION

Briefly stated, the present invention is an electrical conductivity tester and method for accurately measuring the time-varying electrical conductivity $\sigma(t)$ and steady-state electrical conductivity $\sigma_{ss}$ of a test material.

In a first tester embodiment of the present invention, the electrical conductivity tester comprises an oscillator circuit, a probe circuit, and a phase detector circuit. Electrical conductivity is measured by sensing the transmission phase $\theta$ of the probe circuit, which is magnetically coupled with the test material. The transmission phase $\theta$ in the context of this document is the phase difference between the electrical signals entering and leaving the probe circuit. In essence, time-varying conductivity $\sigma(t)$ caused by external stimuli, for example, heat, carrier injection, photon absorption, and mechanical stress, results in a time-varying transmission phase $\theta(t)$ from which the time-varying conductivity $\sigma(t)$ can be determined.

With respect to the first tester embodiment, the oscillator circuit generates a reference oscillator signal. The probe circuit receives the reference oscillator signal and thereby magnetically couples to the test material. Induced currents in the test material modify the phase of the reference oscillator signal in the transmission probe circuit in accordance with the conductivity $\sigma$ of the test material, which is perhaps a steady-state conductivity $\sigma_{ss}$ or a time-varying conductivity $\sigma(t)$. As a consequence, a modified transmission phase signal is derived. Next, a phase detector circuit derives a transmission phase signal, representative of the transmission phase $\theta$, by combining the reference oscillator signal and the modified transmission phase signal. The transmission phase signal is convertible to the conductivity.

In a second tester embodiment of the present invention, the electrical conductivity tester comprises an amplifier connected in a loop-like manner to the probe circuit to form an oscillator circuit. The oscillator circuit generates an oscillator signal in response to the magnetic coupling of the probe circuit with the test material. A frequency discriminator generates a frequency signal from the oscillator signal, the frequency signal being convertible to the conductivity. In addition, a power detection circuit may be disposed to monitor the power absorbed by the probe circuit, thus providing an alternative signal that can be converted to the conductivity. For particular values of test material conductivity, one of the two independently derived signals (frequency shift and absorbed power) may produce a more accurate conductivity measurement.

The present invention overcomes the problems and deficiencies of the prior art, and further provides for the following additional features and advantages.

Another feature of the present invention is that accurate measurements of time-varying transient conductivity $\sigma_{tr}(t)$ can be made with the electrical conductivity tester by suddenly changing the conductivity of the test material via application of an external stimulus of preferably light or some other stimulus, such as heat, carrier injection photon absorption, and mechanical stress. Certain material properties are better determined from measurements of the time-varying transient conductivity $\sigma_{tr}(t)$ of the test material.

Another feature of the present invention is that an electrical conductivity tester and method are provided for accurately measuring total carrier (electrons or holes) lifetime $\tau$, the trap lifetime $\tau_{srh}$, the trap assisted Auger coefficient B, the auger recombination coefficient C, the surface recombination velocity, the energy level corresponding to a trap, and the leakage current of a diode.

Another feature of the present invention is that an electrical conductivity tester is provided which needs only a single coil to measure transient conductivity $\sigma_{tr}(t)$ of a test material.

Another feature of the present invention is that an electrical conductivity tester and method is provided for measuring conductivity at high speeds.

Another feature of the present invention is that an electrical conductivity tester is provided which is insensitive to external interference or noise.

Another feature of the present invention is that an electrical conductivity tester is provided which continuously readjusts for null and eliminates most requirements for manual tuning.

Another feature of the present invention is that an electrical conductivity tester and method are provided for monitoring the quality of semiconducting materials during all phases of manufacture.

Another feature of the present invention is that an electrical conductivity tester is provided which is durable in structure as well as efficient and reliable in operation.

Other objects, features and advantages of the present invention will become apparent from the following description when considered in conjunction with the accompanying drawings.

BRIEF DESCRIPTION OF THE DRAWINGS

The present invention, as defined in the claims, can be better understood with reference to the following drawings.

DETAILED DESCRIPTION OF THE PREFERRED EMBODIMENTS

Figure 1:
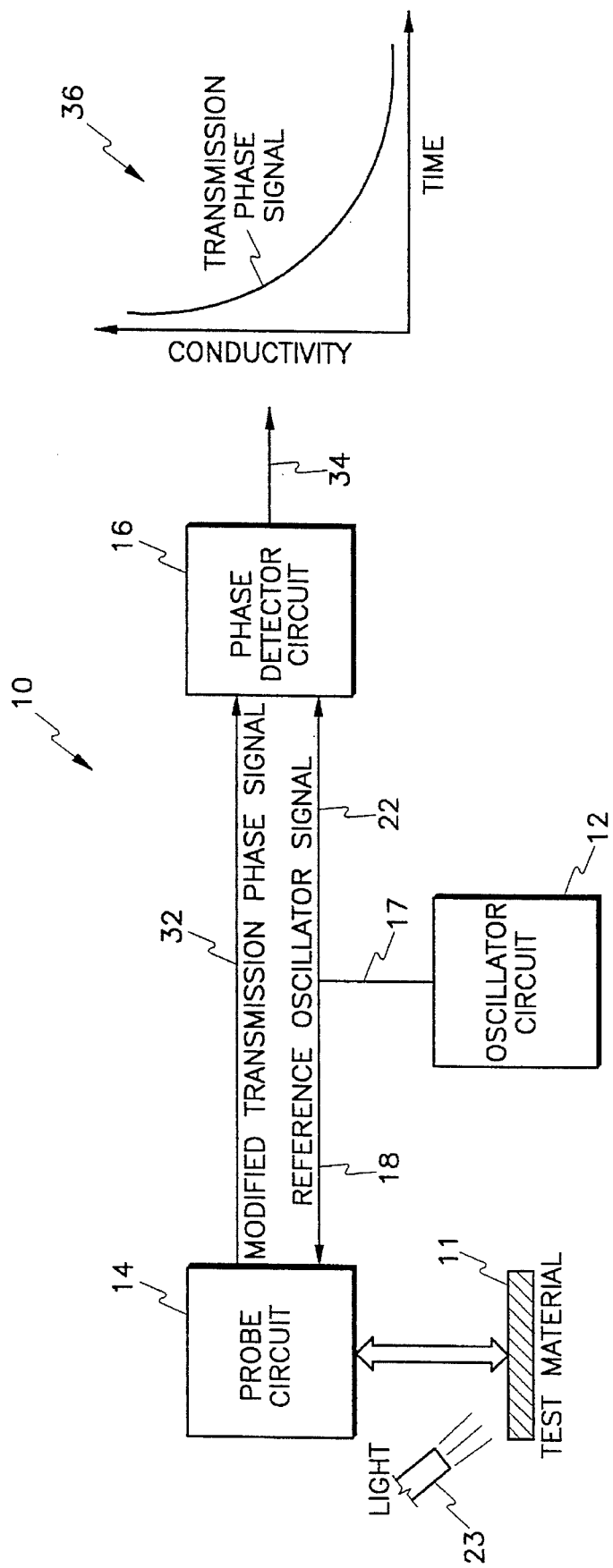
FIG. 1 illustrates a high level block diagram of a first tester embodiment of the present invention.

With reference to the figures wherein like reference numerals designate corresponding parts throughout the several views, an electrical conductivity tester 10 shown in FIG. 1 determines the electrical conductivity $\sigma$, including both time-varying conductivity $\sigma(t)$ and steady-state conductivity $\sigma_{ss}$, of a test material 11 by measuring and monitoring the transmission phase $\theta$ of a probe circuit 14 which is magnetically coupled with the test material 11.

Generally, in structure, the electrical conductivity tester 10 comprises an oscillator circuit 12, a probe circuit 14, and a phase detector circuit 16. The oscillator circuit 12 generates a high frequency, reference oscillator signal 17 which is sent to both the probe circuit 14 and the phase detector circuit 16, as indicated by respective arrows 18, 22. In response to the reference oscillator signal 17, the probe circuit 14 generates a magnetic field that is coupled to a test material 11, for instance, a dielectric, semiconductor, or conductor material. The magnetic field induces eddy currents in the test material 11. The induced eddy currents flowing in the test material 11 are proportional and easily convertible to the conductivity $\sigma$ of the test material 11.

Furthermore, a light source 28, for example, a strobe light, a laser, or other short-duration light propagating device, may be used to project light against the test material 11 in order to measure the time-varying transient conductivity $\sigma_{tr}(t)$ of the test material 11. Upon striking the test material 11, the light generates additional holes and electrons. These holes and electrons temporarily increase the conductivity $\sigma(t)$ of the test material 11. The transient enhancement of the electrical conductivity $\sigma(t)$ under the excitation of light is referred to in the art as the photoconductive effect.

In accordance with the present invention, light projected onto the test material 11 should rapidly rise to a maximum value, should persist for a time period considerably greater than the longest expected carrier lifetime $\tau_{max}$ in the test material, and should fall to zero in a time period much shorter than the smallest anticipated carrier lifetime $\tau_{min}$ the test material. The additional charge carriers produced by the incident light do not persist forever, but once the light is removed, the positive holes and negative electrons recombine thereby returning the test material 11 to a quiescent condition. The excess holes and electrons do not recombine instantaneously, but take some time, typically a few nanoseconds to a few milliseconds, to reduce the carrier concentration of the initial, prelight pulse value. In materials in which a single recombination mechanism dominates, the transient carrier population obeys a simple exponential law and the time for the carrier concentration to decay from its initial value to 1/e (about 37%) of its initial value is called the carrier lifetime $\tau$.

As the conductivity $\sigma(t)$ of the test material 11 increases in response to the incident light, both the physical distribution and the magnitude of the induced eddy currents in the test material 11 change. Electromagnetic energy from the changing eddy currents is magnetically coupled back into the probe circuit 14, thus affecting the transmission phase $\theta(t)$ of the probe circuit 14. In essence, the electrical conductivity tester 10 of the present invention monitors the phase difference, or transmission phase $\theta$, between the reference oscillator signal 18 input to the probe circuit 14 and the modified, possibly time-varying, phase of the modified transmission phase signal 32 leaving the probe circuit 14.

The modified transmission phase signal 32 is sent from the probe circuit 14 to the phase detector circuit 16, as indicated by an arrow 32. Finally, the phase detector circuit 16 derives a transmission phase signal 34, indicative of the transmission phase shift $\theta$, by combining the reference oscillator signal 22 and the modified transmission phase signal 32. The transmission phase signal 34 follows changes of the conductivity $\sigma$ and is proportional to the time-varying conductivity $\sigma(t)$ of the test material 11. Thus, the time-varying conductivity $\sigma(t)$ can easily be derived from the time-varying transmission phase signal 34 as shown by graph 36.

Figure 2:
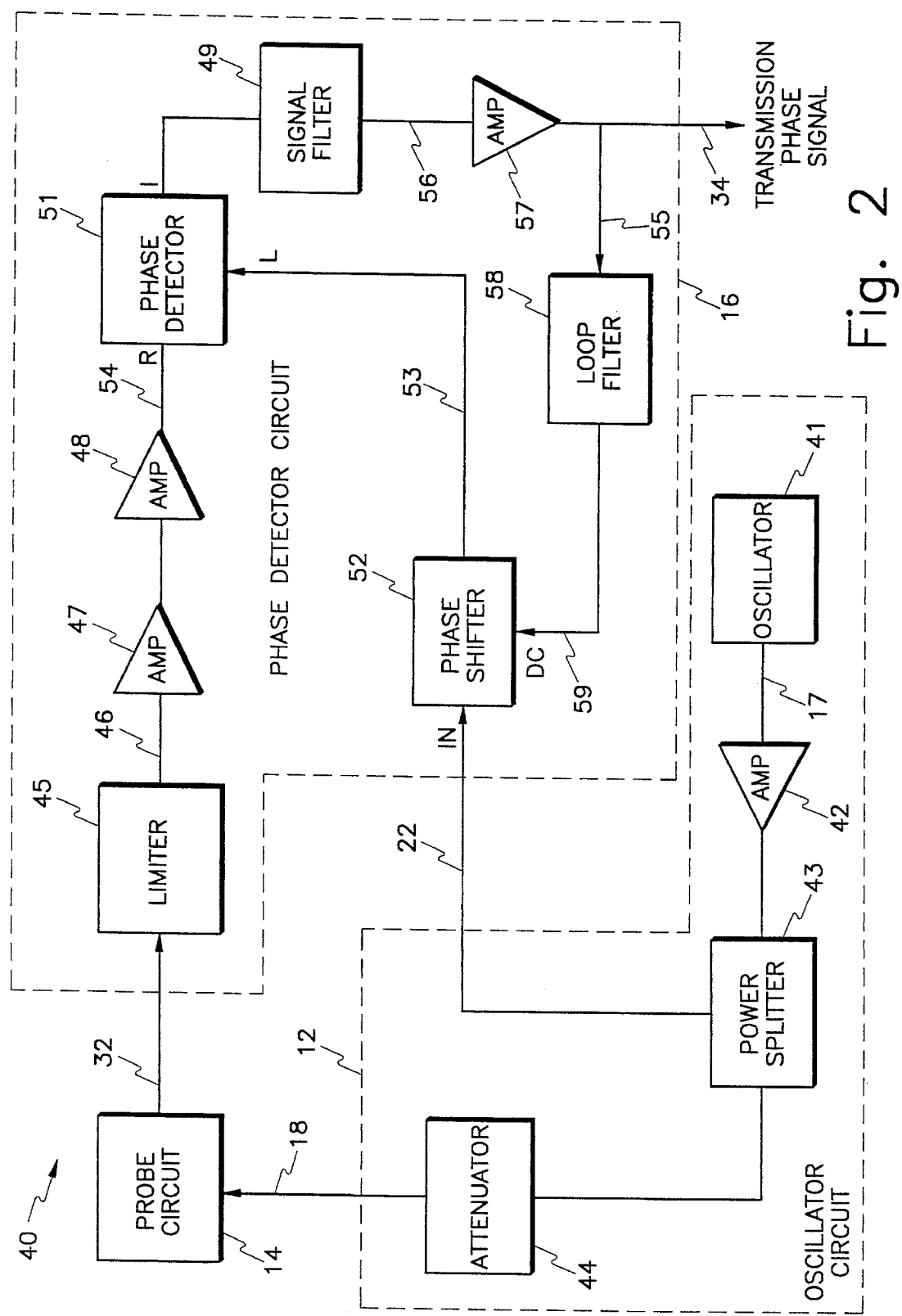
FIG. 2 illustrates a low level block diagram of FIG. 1.

A preferred architecture for the first tester embodiment of the present invention is illustrated in FIG. 2. The preferred architecture, generally denoted as reference numeral 40, comprises examples of specific implementations for the oscillator circuit 12, the probe circuit 14, and the phase detector circuit 16. It should be understood that many other implementations for these circuits 12, 14, 16 are possible and are intended to be within the scope of the present invention.

The oscillator circuit 12 has a high precision modular crystal oscillator 41 operating at a suitable frequency, for example, approximately 100 Megahertz (MHz). There are advantages in some circumstances to use other frequencies because the depth of penetration of the magnetic field varies with frequency. The oscillator 41 feeds the reference oscillator signal 17 to an amplifier 42 which boosts the signal level to approximately 17 dBm. The foregoing signal level is required to properly drive components of the system, such as the phase detector circuit 16. The amplifier output is split into two signal paths by a power splitter 43. Half of the total power (14 dBm) is directed to the probe circuit 14, and the other half is directed to the phase detector circuit 16. An attenuator 44 reduces the power input to the probe circuit 14 to a signal level which insures linear operation of the probe circuit 14.

The function of the probe circuit 14 is primarily to deliver maximum power to its corresponding probe and therefore to the test material 11, while presenting minimum load to the probe. The ultimate sensitivity of the probe circuit 14 is dependent upon resolving phase changes in the probe circuit 14, which are caused by eddy current changes in the test material 11, from the quiescent transmission phase shift of the probe circuit 14. The deleterious effect of the probe circuit 14 on the sensitivity is reduced if the probe circuit 14 absorbs minimum power or has maximum unloaded $Q_u$. When operating as a conductivity tester, the load on the coil is essentially the test material 11, so maximum unloaded $Q_u$ refers to the quality factor Q of the probe circuit 14 in the absence of the test material 11. A high unloaded $Q_u$ can be obtained by using a high-Q L-C resonator, or some other resonator, possibly even a higher Q resonator(s). In conclusion, configuring the probe circuit 14 with a high unloaded quality factor $Q_u$ enables the electrical conductivity tester 40 to be operated with great sensitivity and with a large conductivity range. With the large conductivity range, the test material 11 can comprise a conductor material having an extremely high conductivity ($\sigma \gg 1$) to a dielectric material having an extremely low conductivity ($\sigma \ll 1$).

Before entering the phase-measuring circuit, the modified transmission phase signal 32 from the probe circuit 14 is passed through an amplitude limiter 45. The amplitude limiter 45 is necessary to remove amplitude variations in the modified transmission phase signal 32. In addition to changing the transmission phase, conductivity changes coupled to the probe can also cause variations in the amplitude of the modified transmission phase signal 32. Because the present invention operates by measuring phase differences, it is preferable to remove all amplitude variations from the transmission phase signal 32 if the particular phase detector is sensitive to amplitude variations as well as phase variations. Further, the limited, modified transmission phase signal 46 is then amplified by two cascaded amplifiers 47, 48 to amplify the signal 46 by approximately 13 dB, which provides the requisite 7 dBm signal level for a phase detector 51. The 13 dBm signal is denoted by reference numeral 54 in FIG. 2.

The power splitter 43 of the oscillator circuit 12 provides a reference oscillator signal 22 to a voltage-controlled phase shifter 52 of the phase detector circuit 16. The phase shifter 52 shifts the phase of the reference oscillator signal 22 by approximately 90°. The shifted reference oscillator signal is then forwarded to the phase detector 51, as indicated by arrow 53.

The phase of the signal 54 is compared with the phase of the reference oscillator signal 18 in the phase detector 51 to derive the transmission phase signal 34 indicating the transmission phase $\theta$. Recall that the transmission phase $\theta$ is the phase difference between the electrical signals entering and leaving the probe circuit 14. The phase detector 51 may be constructed in various forms. One simple form that is sensitive to both phase and amplitude is a voltage multiplier. The voltage multiplier can also be constructed in the form of a transconductance multiplier, as is often done in the art of integrated circuit design, or in the form of a balanced modulator (also called "balanced mixer") which are often used in the art of radio and radar receivers. Various other forms of phase detectors can also be derived from interconnections of simple digital gates and memory elements. Significantly, certain of the digital implementations have response characteristics that are sensitive only to phase variations. Such phase detectors have the advantage of eliminating the necessity for a limiter as well as operating over a larger range of phase. However, digital phase detectors presently have an upper frequency limit of less than 100 MHz and are thus restricted in frequency.

For the simple multiplier implementation with sinusoidal excitation, the signal 53 can be expressed as $S_t = V_1 \cos(2\pi ft + \theta)$ and the shifted reference oscillator signal 53 can be expressed as $S_r = V_1 \cos((2\pi ft + 90°)$. As a result of the multiplication function performed by the phase detector 51, the phase detector output signal $S_o = S_t * S_r = V_1 \cos(2\pi ft) * V_1 \sin \theta$.

The phase detector output $S_o$ is passed through a signal filter 49. The signal filter 49 is designed to filter out the second and higher harmonics of the oscillator frequency and other frequencies generated as spurious frequencies within the phase detector 51. The signal filter 49 preferably comprises a low pass filter and a trap filter tuned to the second harmonic of the oscillator frequency. The signal filter 49 does not affect the base-band (DC to the oscillator frequency) of the transmission phase signal 34. The filtered transmission phase signal 56 is then increased in signal level by a wide-bandwidth amplifier 57. The output of this wide-bandwidth amplifier 57 is split into two branches 34, 55. A first branch 34 is the time-varying transmission phase signal 34, which is the primary focus of analysis herein. A second branch 55 is sent through a loop filter 58 and then to the control input 59 of a phase shifter 52.

Viewed collectively, the phase detector 51, wide-bandwidth amplifier 57, loop filter 58, and phase shifter 52, comprise an automatic feedback control system. The feedback control system acts to reduce the average phase difference i.e., the transmission phase signal 34, to zero by shifting the phase of reference oscillator signal 22 to the phase of the phase detector 51 to compensate for the phase error. The ability of the feedback control system to reduce the phase difference is dependent upon the mathematical transfer function of the loop filter 58. In the present invention, the loop filter 58 is designed to cause the feedback control system to remove slowly-varying changes in the transmission phase signal 34. Thus, the phase shifter control voltage 59 is a measure of the average transmission phase $\theta$ and hence the average or steady-state conductivity $\sigma_{ss}$, while the amplifier output 34, taken before the loop filter 58, is a measure of the instantaneous transmission phase $\theta$ and hence instantaneous conductivity $\sigma$. Accordingly, the present invention is able to measure both the steady-state conductivity $\sigma_{ss}$ and the time-varying conductivity $\sigma(t)$.

The foregoing feedback control system 51, 49, 57, 58, 52 continuously readjusts the electrical conductivity tester 40 to an average phase null. This action automatically removes component drift and setup variations from the measurement. Also, this action eliminates the need for continuous manual readjustment in response to changing experimental conditions.

Any conventional data monitoring device (not shown) calibrated in units of carrier density or conductivity can be directly connected to the transmission phase signal 34. For example, data acquisition for the electrical conductivity tester 40 can be accomplished with an oscilloscope or with a suitable data acquisition card inserted into a conventional personal computer.

Figure 3A:
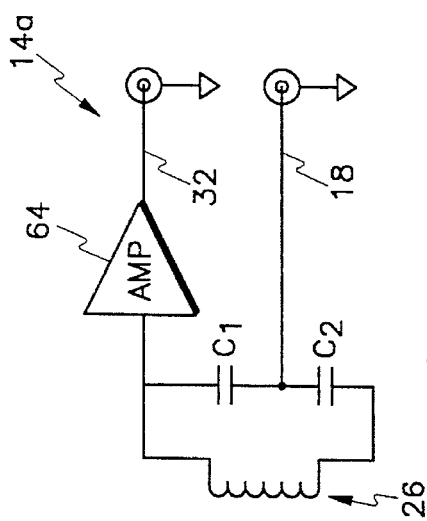
FIG. 3A illustrates a first probe circuit embodiment of the probe circuit shown in FIG. 1, 2.

FIGS. 3A–3D schematically illustrate examples of specific probe circuit embodiments for the probe circuit 14 of FIGS. 1, 2. A first probe circuit embodiment 14a of the probe circuit 14 is shown in FIG. 3A. The first probe circuit embodiment 14a is an L-C resonator 14a having a high unloaded quality factor $Q_u$. As illustrated in FIG. 3A, the first probe circuit embodiment comprises a probe coil 26, two capacitors $C_1$, $C_2$ and an amplifier 64. The amplifier 64, which can merely be an amplifying transistor, is designed to exhibit a high input impedance, or low input admittance, and thus minimize loading of the L-C resonator 14a. The amplifier 64 isolates the limiter 45 of FIG. 2 as well as subsequent circuit elements of the electrical conductivity tester 40 from the L-C resonator 14a. This isolation removes the loading effect of these circuit elements and increases the loaded quality factor Q of the L-C resonator 14a. The imaginary part of the input admittance of the amplifier 64 is combined with the circuit elements of the L-C resonator 14a and therefore does not adversely affect the operation of the L-C resonator 14a. Furthermore, the capacitance values of capacitors $C_1$, $C_2$ are selected to provide a proper impedance match to the attenuator 44 of FIG. 2, while at the same time allowing the unloaded quality factor $Q_u$ of the L-C resonator 14a to have the largest practicable value. It should be noted that, although not shown, an amplifier similar to amplifier 64 may be connected to the other probe circuit embodiments for the probe circuit 14, discussed in detail hereinbelow, so as to aid in further reducing the loading of subsequent circuit elements.

Figure 3B:
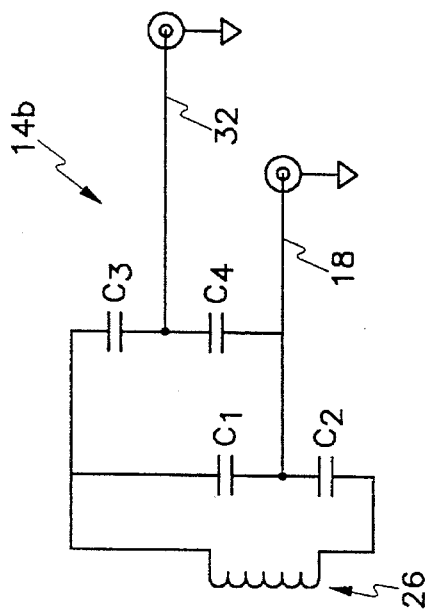
FIG. 3B illustrates a second probe circuit embodiment of the probe circuit shown in FIG. 1, 2.

A second probe circuit embodiment 14b of the probe circuit 14 is illustrated in FIG. 3B. The second probe circuit embodiment 14b is also an L-C resonator. The second probe circuit embodiment 14b comprises the probe coil 26 and capacitors $C_1$–$C_4$. The capacitors $C_1$–$C_4$ are disposed to counterbalance the inductive susceptance introduced by the probe coil 26 while matching impedances, thereby allowing the largest practicable unloaded quality factor $Q_u$.

Figure 3C:
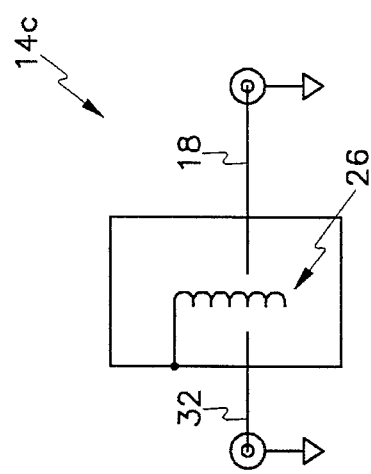
FIG. 3C illustrates a third probe circuit embodiment of the probe circuit shown in FIG. 1, 2.

A third probe circuit embodiment 14c of the probe circuit 14 is shown in FIG. 3C. The third probe circuit embodiment 14c is a helical resonator having a very high unloaded quality factor $Q_u$. In fact, the unloaded quality factor $Q_u$ of the helical resonator 14c is greater than the unloaded quality factor $Q_u$ of any conventional L-C resonator by a factor of about tenfold or more. The helical resonator 14c can tremendously enhance the sensitivity and range of the electrical conductivity tester 10, 40 in accordance with the present invention.

Figure 3D:
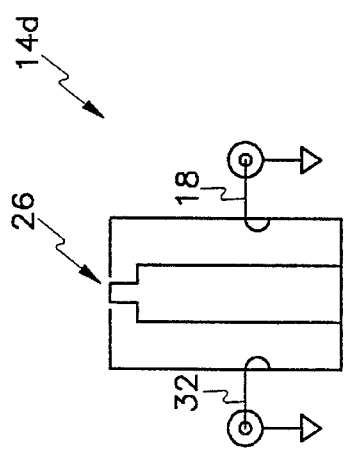
FIG. 3D illustrates a fourth probe circuit embodiment of the probe circuit shown in FIG. 1, 2.

A fourth probe circuit embodiment 14d of the probe circuit 14 is shown in FIG. 3D. The fourth probe circuit embodiment 14d comprises essentially a cavity resonator. The cavity resonator 14d can take various conventional configurations. However, a cavity resonator suitable for the purpose herein is disclosed in U.S. Pat. No. 3,953,796 to Keller, which disclosure is incorporated herein by reference. The cavity resonator 14d enables very high frequency operation of the electrical conductivity tester 10, 40.

Figure 4:
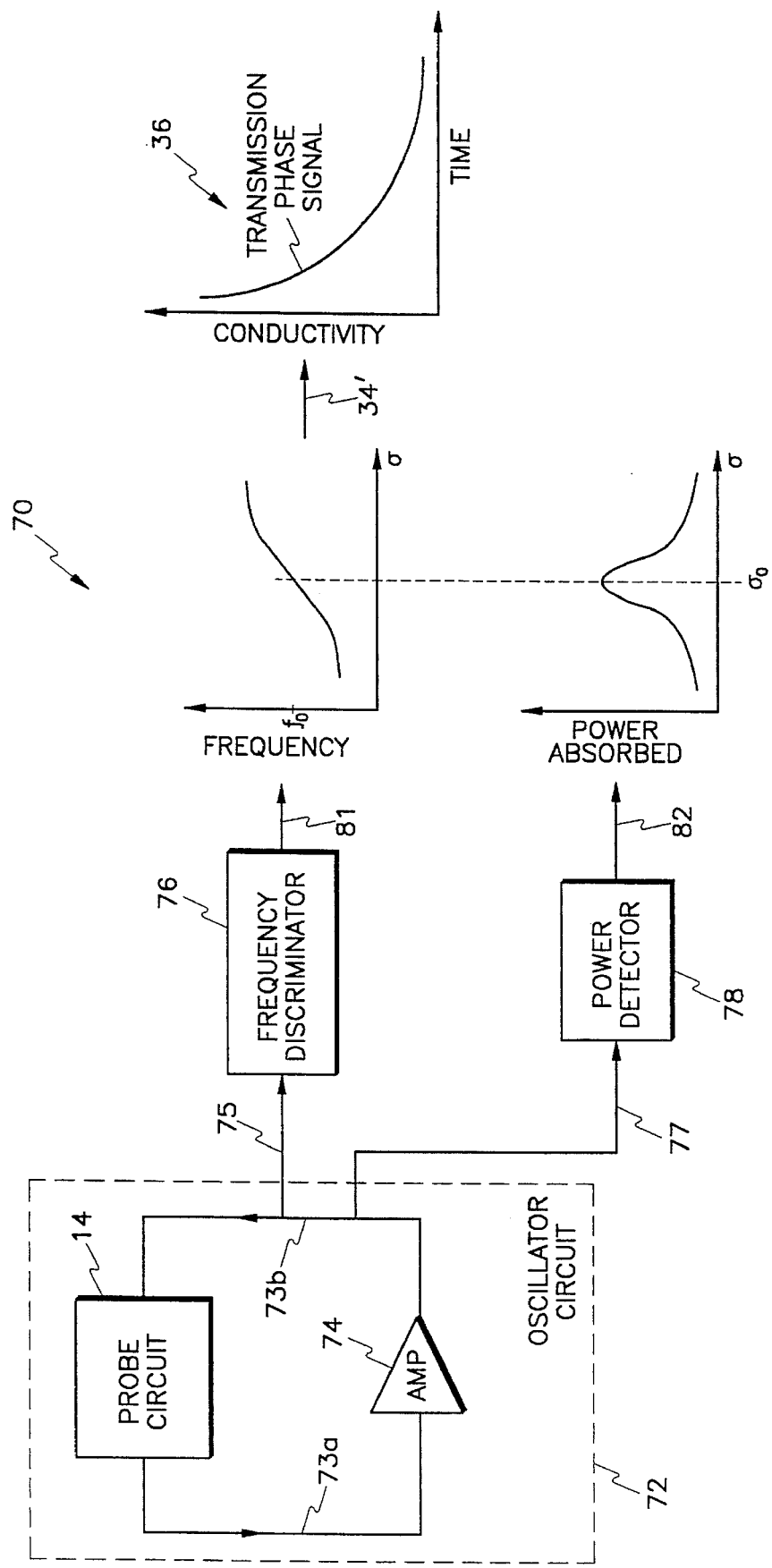
FIG. 4 illustrates a high level block diagram of a second tester embodiment of the present invention.

FIG. 4 illustrates a second tester embodiment of the electrical conductivity tester in accordance with the present invention. The second tester embodiment of the electrical conductivity tester, generally denoted by reference numeral 70, comprises an oscillator circuit 72 derived from the probe circuit 14 and an amplifier 74, both connected in a loop-like manner to derive an oscillator loop 73. The oscillator circuit 72 oscillates at the frequency at which the phase shift around the loop 73 is zero degrees. The zero phase shift frequency depends upon the signal induced in the probe coil 26 by the test material 11 and, accordingly, the frequency of oscillation depends upon the conductivity of the test material 11. Preferably, the probe circuit 14 comprises the helical resonator 14c shown in FIG. 3C, because of its high unloaded quality factor $Q_u$ and sensitivity. However, many other implementations are possible, including those shown in FIGS. 3A–3D.

A frequency discriminator 76 is disposed to monitor the frequency signal 75 from the oscillator circuit 72 and particularly the frequency of the frequency signal 75. The frequency discriminator 76 preferably comprises a phase locked loop (PLL) detector wherein the voltage-controlled oscillator control signal would be a measure of the frequency of oscillation. As indicated in FIG. 4 by the graph at the frequency discriminator output 81, the frequency of oscillation changes more for test materials 11 of high conductivity than for test materials 11 of low conductivity. Conductivity information is recovered as indicated by an arrow 34' via a frequency shift versus conductivity calibration table prepared by measuring test materials 11 with independently determined conductivities The power absorbed by the probe circuit 14 also depends upon the conductivity of the test material 11. Accordingly, in the second tester embodiment, a directional coupler (not shown) may be disposed to sample the power absorbed by the probe circuit 14 and to deliver the power sample 77 to a power detector 78 which converts the power sample 77 to a displayable power signal 82. Further, in the second tester embodiment 70, the frequency signal 81 and a power signal 82 may be used together or separately to recover the time-varying conductivity σ(t) of the test material 11. It is worth noting that having both frequency and power information removes a possible ambiguity in the conductivity value which exists when the conductivity σ is determined by measurement of the power response alone. This ambiguity is apparent in FIG. 4 by examination of the bell-shaped power response curve at the output 82.

By measuring the time-varying transient conductivity $\sigma_{tr}(t)$ of the test material 11 in accordance with the principles of the present invention, many important characteristics of the test material 11 can be determined. For example, the following characteristics can be determined using the electrical conductivity tester 10, 40: total carrier (electrons or holes) lifetime τ, the trap lifetime $\tau_{srh}$, the trap assisted Auger coefficient B, the auger recombination coefficient C, the surface recombination velocity, the energy level corresponding to a trap, and the leakage current of a diode.

In order to compute the carrier parameters, i.e., the total carrier lifetime τ, the trap lifetime $\tau_{srh}$, the trap assisted Auger recombination coefficient B, and the Auger recombination coefficient C, the transient transmission phase signal 34 is first converted to time-varying conductivity and then to time-varying carrier concentration N. Total carrier lifetime τ at various carrier injection levels N is determined from the following formula:

$$\frac{1}{\tau} = -\frac{1}{N} \frac{dN}{dt}$$

The τ vs. N data are curve fitted to the following well known formula to obtain $\tau_{srh}$, B, and C.

$$\frac{1}{\tau} = \frac{1}{\tau_{srh}} + BN + CN^2$$

The process by which the data points from the transient transmission phase signal 34 are curve fitted into the above equation is well known in the art and is described in the following documents, which are incorporated herein by reference: S. K. Pang & A. Rohatgi, "Record High Recombination Lifetime and Oxidized Magnetic Czochralski Silicon," *Appl. Phys. Lett.*, Volume 59, No. 2, 8 Jul. 1991; T. F. Ciszek, T. Wang, T. Schuyler, and A. Rohatgi, "Some Effects of Crystal Growth Parameters on Minority Carrier Lifetime in Float-Zoned Silicon," *J. Electrochem. Soc.*, Volume 136, No. 1, January 1989; and S. K. Pang and A. Rohatgi, "Effect of Oxygen Concentration on Lifetime in Magnetic Czochralski Silicon," *J. Electrochem. Soc.*, Volume 138, No. 2, February 1991.

It will be obvious to those skilled in the art that many variations may be made to the preferred embodiments described above without departing from the novel teachings of the present invention. All such variations are intended to be incorporated herein and within the scope of the present invention.

Wherefore, the inventors claim the following:

1. An electrical conductivity tester for accurately measuring the time-varying conductivity and steady-state conductivity of a test material, comprising:

an oscillator means for generating a reference oscillator signal;

a single probe coil means for receiving said reference oscillator signal, for magnetically coupling to said test material, and for modifying said reference oscillator signal via electromagnetic induction to derive a modified transmission phase signal;

a phase detector means for deriving a transmission phase signal indicative of a phase difference by comparing said reference oscillator signal to said modified transmission phase signal, said transmission phase signal being convertible to said time varying conductivity; and means for averaging said transmission phase signal over time and for generating an average phase signal, said average phase signal being convertible to steady-state conductivity of said test material.

2. The electrical conductivity tester of claim 1, wherein said probe means comprises a combination of two series-connected capacitors in parallel with an inductor, said combination connected in series with an amplifier.

3. The electrical conductivity tester of claim 1, wherein said probe means comprises a cavity resonator.

4. The electrical conductivity tester of claim 1, wherein said probe means comprises a helical resonator.

5. The electrical conductivity tester of claim 1, wherein said test material comprises a semiconductor.

6. The electrical conductivity tester of claim 1, further comprising a phase shifter means for administering a phase shift to said reference oscillator signal before comparing said reference oscillator signal to said modified transmission phase signal.

7. The electrical conductivity tester of claim 1, further comprising an adjustable attenuator and an amplifier in series with said oscillator means, said adjustable attenuator for permitting adjustment of the power level of said reference oscillator signal.

8. The electrical conductivity tester of claim 1, further comprising a light source for directing light against said test material.

9. The electrical conductivity tester of claim 6, wherein said averaging means comprises feedback means for filtering said transmission phase signal to derive said average phase signal and for forwarding said average phase signal to said phase shifter means, said feedback means and said phase shifter means for adjusting a phase of said reference oscillator signal so that said transmission phase signal is reduced to zero with a steady-state conductivity.

10. The electrical conductivity tester of claim 6, wherein said phase shift is approximately ninety degrees when said transmission phase signal is equal to zero.

11. A method for accurately determining the time varying conductivity and steady-state conductivity of a test material, the method comprising the steps of:

sending a reference oscillator signal to a single probe coil means;

magnetically coupling said reference oscillator signal and said test material with said single probe coil means to derive a modified transmission phase signal;

comparing said reference oscillator signal to said modified transmission phase signal to derive a transmission phase signal indicative of a phase difference, said transmission phase signal being convertible to said time-varying conductivity; and averaging said transmission phase signal to determine an average phase signal, said average phase signal being convertible to said steady-state conductivity of said test material.

12. The method of claim 11, further comprising the steps of exciting said test material with light and measuring a time-varying transient conductivity of said test material based upon said transmission phase signal.

13. The method of claim 11, wherein said step of averaging comprises the steps of:

filtering said transmission phase signal to derive said average phase signal; and using said average phase signal to adjust a phase of said reference oscillator signal so that said transmission phase signal is reduced to zero with a steady-state conductivity.

14. The electrical conductivity tester of claim 1, wherein said time-varying conductivity is a transient conductivity induced in said solid test material by a short-duration light source.

15. The method of claim 11, further comprising the step of removing said solid test material from the light source in order to determine the time-varying conductivity recognized as transient conductivity.

16. An electrical conductivity tester for accurately measuring the conductivity of a test material, comprising:

an oscillator means for generating a reference oscillator signal;

a probe means for receiving said reference oscillator signal, for magnetically coupling to said test material, and for modifying said reference oscillator signal via electromagnetic induction to derive a modified transmission phase signal;

a phase detector means for deriving a transmission phase signal by comparing said reference oscillator signal to said modified transmission phase signal, said transmission phase signal being convertible to said conductivity; and a feedback means for filtering said transmission phase signal to derive an average transmission phase signal and for forwarding said average transmission phase signal to said phase detector means, said feedback means and said phase detector means for adjusting a phase of said reference oscillator signal so that said transmission phase signal is reduced to zero with a steady-state conductivity.

17. The electrical conductivity tester of claim 16, wherein said probe means comprises a combination of two series connected capacitors in parallel with an inductor, said combination connected in series with an amplifier.

18. The electrical conductivity tester of claim 16, wherein said probe means comprises a cavity resonator.

19. The electrical conductivity tester of claim 16, wherein said probe means comprises a helical resonator.

20. The electrical conductivity tester of claim 16, wherein said test material comprises a semiconductor.

21. The electrical conductivity tester of claim 16, further comprising a phase shifter means for administering a phase shift to said reference oscillator signal before comparing said reference oscillator signal to said modified transmission phase signal.

22. The electrical conductivity tester of claim 16, further comprising an adjustable attenuator in an amplifier in series with said oscillator means, said adjustable attenuator for permitting adjustment of the power level of said reference oscillator signal.

23. The electrical conductivity tester of claim 16, further comprising a light source for directing light against said test material.

24. The electrical conductivity tester of claim 21, wherein said phase shift is approximately 90° when said average transmission phase signal is equal to zero.

25. The electrical conductivity tester of claim 16, wherein said probe means comprises a single probe coil configured to magnetically couple to said test material.

26. A method for accurately determining the conductivity of a test material, the method comprising the steps of:

sending a reference oscillator signal to a probe circuit;

magnetically coupling said reference oscillator signal and said test material to derive a modified transmission phase signal;

comparing said reference oscillator signal to said modified transmission phase signal to derive a transmission phase signal, said transmission phase signal being convertible to said conductivity;

filtering said transmission phase signal to derive an average transmission phase signal; and using said average transmission phase signal to adjust a phase of said reference oscillator signal so that said transmission phase signal is reduced to zero with a steady-state conductivity.

27. The method of claim 26, further comprising the step of exciting said test material with light.

28. The method of claim 26, further comprising the step of using a cavity resonator in said probe circuit for magnetically coupling said reference oscillator signal and said test material.

29. The method of claim 26, further comprising the step of using a helical resonator in said probe circuit for magnetically coupling said reference oscillator signal and said test material.

30. The method of claim 26, wherein said step of magnetically coupling said reference oscillator signal and said test material comprises the step of coupling said reference oscillator signal to a semiconductor material.

31. The method of claim 26, further comprising the step of administering a phase shift to said reference oscillator signal before comparing said reference oscillator signal with said modified transmission phase signal.

32. The method of claim 26, further comprising the step of adjusting the power level of said reference oscillator signal.

33. The method of claim 26, further comprising the step of directing light against said test material.

34. The method of claim 26, further comprising the step of filtering said transmission phase signal to derive an average transmission phase signal.

35. The method of claim 26, further comprising the step of adjusting a phase of said reference oscillator signal so that said transmission phase signal is reduced to zero with a steady-state conductivity.

* * * * *

UNITED STATES PATENT AND TRADEMARK OFFICE
CERTIFICATE OF CORRECTION

PATENT NO. : 5,508,610
DATED : April 16, 1996
INVENTOR(S) : Feeney et al.

It is certified that error appears in the above-indentified patent and that said Letters Patent is hereby corrected as shown below:

Column 11, line 20, insert ----- before "varying."

Column 11, line 24, insert --said-- before "steady-state."

Column 11, line 60, insert ----- before "varying."

Column 14, line 16, delete "with" and replace with --to--.

Signed and Sealed this

Thirteenth Day of August, 1996

Attest:

BRUCE LEHMAN

*Attesting Officer*  *Commissioner of Patents and Trademarks*